United States Patent
Chung et al.

(10) Patent No.: US 8,784,630 B2
(45) Date of Patent: Jul. 22, 2014

(54) SAMPLE STACKING METHOD USING ON-LINE AUTOMATIC SOLID PHASE EXTRACTION COUPLED TO NONAQUEOUS CAPILLARY ELECTROPHORESIS AND INTERFACE STRUCTURE BETWEEN SOLID-PHASE PRECONCENTRATION CARTRIDGE AND CAPILLARY THEREFOR

(75) Inventors: Doo Soo Chung, Seoul (KR); Lichun Liu, Seoul (KR); Kihwan Choi, Seoul (KR)

(73) Assignees: Samsung Electronics Co., Ltd. (KR); Seoul National University Industry Foundation (KR)

( * ) Notice: Subject to any disclaimer, the term of this patent is extended or adjusted under 35 U.S.C. 154(b) by 624 days.

(21) Appl. No.: 12/206,221

(22) Filed: Sep. 8, 2008

(65) Prior Publication Data
US 2009/0084680 A1 Apr. 2, 2009

(30) Foreign Application Priority Data
Sep. 28, 2007 (KR) .................. 10-2007-0097723

(51) Int. Cl.
*G01N 27/453* (2006.01)
(52) U.S. Cl.
USPC .................................. 204/600; 204/451
(58) Field of Classification Search
USPC ............ 204/450, 451, 600–621, 641–645; 210/198, 656
See application file for complete search history.

(56) References Cited

U.S. PATENT DOCUMENTS

2007/0111329 A1* 5/2007 Guzman ................. 436/518

OTHER PUBLICATIONS

Beattie et al., The use of solid phase concentrators for on-line preconcentration of metallothionein prior to isoform separation by capillary zone electrophoresis, Electrophoresis, 1995, 322-328.*
Baryla et al., Analyst, 2003, 128, 1009-1012.*
Peterson et al. J. Chromatography A, 1999, 841, 249-261.*
Saito et al. Anal Bioanal Chem. 2002, 372, 164-168.*
Puig et al. Recent advances in coupling solid-phase extraction and capillary electrophoresis (SPE-CE), Trends in Analytical Chemistry, vol. 26, 2007, 664-678.*
Strausbauch et al., Concentration and separation of hypoglycemic drugs using solid-phase extraction-capillary electrophoresis, J. of Chromatography A, 1995, 717, 279-29.*

* cited by examiner

*Primary Examiner* — Luan Van
*Assistant Examiner* — Gurpreet Kaur
(74) *Attorney, Agent, or Firm* — Cantor Colburn LLP

(57) ABSTRACT

A sample stacking method using on-line automatic solid phase extraction coupled to nonaqueous capillary electrophoresis, and an interface structure between a solid-phase preconcentration cartridge and a capillary therefor. The sample analysis method using solid phase extraction coupled to nonaqueous capillary electrophoresis by connecting a solid-phase preconcentration cartridge with a capillary includes: extracting a sample on a solid phase; injecting an elution solvent at an outlet terminal of the capillary, the elution solution desorbing analytes adsorbed onto a solid-phase material of a solid-phase preconcentration cartridge; and injecting a nonaqueous buffer solution from the outlet terminal of the capillary to push the elution solvent to the solid-phase material.

3 Claims, 3 Drawing Sheets

SAMPLE STACKING METHOD USING ON-LINE AUTOMATIC SOLID PHASE EXTRACTION COUPLED TO NONAQUEOUS CAPILLARY ELECTROPHORESIS AND INTERFACE STRUCTURE BETWEEN SOLID-PHASE PRECONCENTRATION CARTRIDGE AND CAPILLARY THEREFOR

This application claims priority to Korean Patent Application No. 2007-97723, filed on Sep. 28, 2007, and all the benefits accruing therefrom under 35 U.S.C. §119, the contents of which in their entirety are herein incorporated by reference.

BACKGROUND OF THE INVENTION

1. Field of the Invention

This disclosure is directed to a sample stacking method using on-line automatic solid phase extraction coupled to nonaqueous capillary electrophoresis, and an interface structure between a solid-phase preconcentration cartridge and a capillary therefor. In particular, the method is directed to a technique for significantly enhancing sensitivity in the analysis of a sample by coupling a solid-phase preconcentration cartridge to a capillary, desorbing the extracted sample with a large amount of an organic solvent, and then applying field-amplified sample stacking.

2. Description of the Related Art

In order to overcome a low detection limit of capillary electrophoresis, various methods based on electrophoresis and chromatography have been developed. The methods based on electrophoresis are methods for stacking a sample according to a difference in the mobility of the sample in discontinuous regions. The methods are advantageous in that no other special equipment is required. However, there is a disadvantage in that an additional purification process is necessary for its application to a complex sample. That is, since an additional process is required to prepare a sample, there is a problem of efficiency caused by using the methods for stacking the sample according to a difference in the mobility of the sample in discontinuous regions.

On the other hand, the methods using chromatography are methods for stacking a sample by adsorbing a large amount of the sample onto a stationary phase. The methods are advantageous in that simultaneous purification and stacking of the sample is possible. Among the methods using chromatography, solid phase extraction is most frequently used, and the basic principle of the method is as follows. When a large amount of a solution containing a sample is passed through a sorbent, the sample is adsorbed onto the sorbent. At this time, the substances in the sample solution which did not adsorb onto the sorbent are passed through, thereby allowing purification of the sample. Then, the sample is desorbed with a small volume of an elution solvent for sample stacking. If the sample is not lost during desorption, it is possible to stack the sample in the same volume ratio as the sample solution and the elution solvent. However, the volume of the solution to be injected into capillary electrophoresis is at a nanoliter level. Thus, in general, only a partial amount of the elution solvent is injected, and most of the adsorbed sample is not analyzed. There are various methods to couple solid phase extraction to capillary electrophoresis. One method includes directly connecting a solid-phase preconcentration cartridge to a capillary. This method can be applied to a typical capillary electrophoresis machine. Thus, the method is easily automatized. However, when desorption is carried out with a large amount of a solvent, the stacking efficiency is decreased resulting in no separation between the sample. Therefore, the amount of the desorption solvent is limited to a several nanoliter level, resulting in a disadvantage in that a large amount of the sample remains on the sorbent. Thereby, the residual sample influences the subsequent experiment. In short, when the sample is desorbed with an insufficient amount of the elution solvent, most of the analytes remain in the solid phase causing problems. When the sample is desorbed with a large amount of the elution solvent, there are problems of dilution and deteriorated separation.

In solid phase extraction, a polyethylene sleeve or the like is charged with a packing material and the packing material is fixed with glass fibers. The sleeve is connected between a capillary, which is cut in the middle, and adhered. Thus, these adhered substances may dissolve in a solvent resulting in decreased stability. The sleeve may be formed longer to adhere with the capillary more stably. However, in this case, one end of the connected capillary must be shortened, thereby having restrictions in installing the capillary in a commercialized capillary electrophoresis ("CE") machine. Moreover, there is a problem in having to connect the capillary at both ends of the sleeve in addition to having a difficulty in packing the material inside the sleeve. Since one end of the capillary is shorter as mentioned above, a large amount of solvent cannot be flowed therethrough. Thus, a significant amount of analytes remain in the solid phase. This can also cause a problem of deteriorating the electrophoretic ability by having the residual analytes in the solid phase elute during the analysis.

BRIEF SUMMARY OF THE INVENTION

Disclosed herein is an exemplary embodiment of a sample analytic method by coupling solid phase extraction to capillary electrophoresis. The exemplary method solves a problem caused by analytes remaining in the solid phase when using a small amount of an elution solvent, a structural problem for being unable to use a large amount of an elution solvent, and a problem of deteriorating electrophoretic ability caused by the decreased stacking efficiency when using a large amount of an elution solvent.

Meanwhile, a large amount of the elution solvent is used to carry out desorption, provided that the desorbed sample is stacked to further improve the detection sensitivity, thereby allowing detection of the analytes at a very low level of concentration. Such elution, stacking and analysis are performed automatically at the same time such that the procedure is simplified and the duration time is shortened.

Also disclosed herein is an interface structure between a capillary and a solid-phase preconcentration cartridge for suitably realizing the above method.

In one exemplary embodiment, a sample analysis method using solid phase extraction coupled to nonaqueous capillary electrophoresis by connecting a solid-phase preconcentration cartridge to a capillary is provided. The method includes: extracting a sample on a solid phase; injecting an elution solvent at an outlet terminal of the capillary, the elution solution capable of desorbing analytes adsorbed onto a solid-phase material of a solid-phase preconcentration cartridge; and injecting a nonaqueous buffer solution at the outlet terminal of the capillary to push the elution solvent to the solid-phase material.

In another exemplary embodiment, an interface structure between a solid-phase preconcentration cartridge and a capillary for analyzing a sample by coupling solid phase extraction to capillary electrophoresis is provided. The solid-phase preconcentration cartridge has a tubing sleeve, and the sleeve is packed with a solid-phase material. The structure has an injection part of the capillary inserted into the tubing sleeve at one end opposite from the other end where the sample is injected into the tubing sleeve.

The simple and convenient interface structure between a solid-phase preconcentration cartridge and a capillary is disclosed. In addition, solid phase extraction coupled to nonaqueous capillary electrophoresis and field amplified sample stacking is disclosed. Therefore, the analytes adsorbed onto the solid-phase material are desorbed with a large amount of the elution solvent, and the desorbed sample is stacked to allow sample analysis at a very low concentration.

BRIEF DESCRIPTION OF THE DRAWINGS

Exemplary embodiments will be more clearly understood from the following detailed description taken in conjunction with the accompanying drawings, in which.

DETAILED DESCRIPTION OF THE INVENTION

Figure 1:
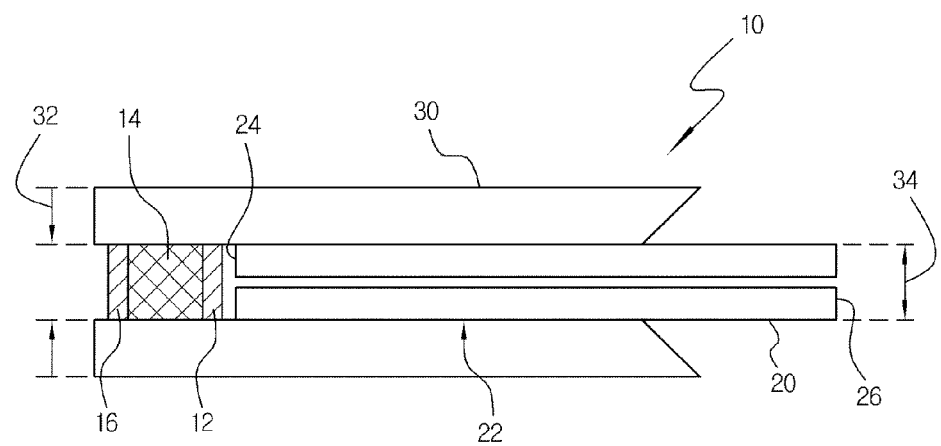
FIG. 1 is a schematic diagram illustrating an on-line solid-phase preconcentration cartridge coupled to a separation capillary.

The invention is described more fully hereinafter with reference to the accompanying drawings, in which exemplary embodiments of the invention are shown. The present invention may, however, be embodied in many different forms and should not be construed as being limited to the embodiments set forth herein. Rather, these embodiments are provided so that this disclosure will be thorough and complete, and will fully convey the scope of the invention to those skilled in the art. Like reference numerals refer to like elements throughout.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the present invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another elements as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower", can therefore, encompasses both an orientation of "lower" and "upper," depending on the particular orientation of the figure. Similarly, if the device in one of the figures is turned over, elements described as "below" or "beneath" other elements would hen be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Hereinafter, exemplary embodiments of the present invention will be described in further detail with reference to the accompanying drawings.

According to one exemplary embodiment, a sample analysis method using solid phase extraction coupled to nonaqueous capillary electrophoresis by connecting a solid-phase preconcentration cartridge to a capillary comprises: extracting a sample on a solid phase; injecting an elution solvent, capable of desorbing analytes adsorbed onto a solid-phase material of a solid-phase preconcentration cartridge, at an outlet terminal of the capillary; and injecting a nonaqueous buffer solution at the outlet terminal of the capillary to push the elution solvent to the solid-phase material portion.

In another exemplary embodiment, the elution solvent may be provided in an amount sufficient to desorb the entire analytes adsorbed onto the solid-phase material.

In another exemplary embodiment, the method may further comprise applying an electric field to pass the elution solvent through the solid-phase material for desorption of the analytes and stacking of the analytes at the interface of the elution solvent and the buffer solution.

In another exemplary embodiment, the solid-phase preconcentration cartridge coupled to the capillary may have a tubing type sleeve, the sleeve being packed with a solid-phase material, and an interface having an injection part of the capillary inserted into the tubing sleeve at one end opposite from the other end where the sample is injected into the tubing sleeve.

In another exemplary embodiment, an interface structure between a solid-phase preconcentration cartridge and a capillary for analyzing a sample by coupling solid phase extraction to capillary electrophoresis is provided, in which the solid-phase preconcentration cartridge has a tube-type sleeve, and the sleeve is packed with a solid-phase material. The structure has an injection part of the capillary inserted into the tubing sleeve at one end opposite from the other end where the sample is injected into the tubing sleeve.

In another exemplary embodiment, a length of the capillary inserted into the tubing sleeve is at least 3 times the outside diameter of the capillary and the inside diameter of the tubing is smaller than the outside diameter of the capillary to be inserted.

Exemplary embodiments of the present invention couple the solid-phase preconcentration cartridge to the capillary, desorb the extracted sample with a large amount of an organic solvent, and then apply field amplified sample stacking to significantly improve sensitivity in the analysis of the sample.

First, improvement on the connection interface of the solid phase and the capillary will be described. FIG. 1 is a schematic diagram of an on-line solid-phase preconcentration cartridge 10 coupled to a separation capillary 20. In the case of conventionally installing a solid phase extraction part in the middle of a capillary, a sleeve part which connects the capillary is not sufficiently long enough to equip the coupled solid-phase preconcentration cartridge and capillary in a commercialized machine. In exemplary embodiments, one end of the capillary 20 is connected to the solid-phase preconcentration cartridge 10, thereby ensuring a sufficiently long capillary. In addition, a connection part 22 of the capillary 20 and a tubing sleeve 30 is formed long enough such that stability may be provided at the connection part 22. As the sleeve 30, Teflon<R> tubing or the like may be used. In this case, an additional adhesive is not necessary when using Teflon<R> tubing as the sleeve 30 having an inner diameter 32 smaller to some extent than an outer diameter 34 of the capillary 20. When inserting the capillary 20 into the tubing sleeve 30, a sufficient length of the capillary 20 must be inserted into the sleeve 30 so as to have a stable adhesion between the capillary 20 and the tubing 30. In exemplary embodiments, a length of the capillary 20 to be inserted is at least 3 times the outer diameter 34 of the capillary 20, or the length may be several ten-folds. This is because, the solid phase extraction part 10 is connected at an injection part 24 of the capillary 20 instead of the middle of the capillary, and if so, there is no loss of length in the capillary 20.

Inside Teflon<R> tubing 30, a frit 12, like a glass fiber, is inserted, a solid-phase material 14 to which analyst is to be adsorbed is packed, and then another frit 16 is inserted to complete the solid-phase preconcentration cartridge 10. If the solid-phase material 14 is packed in a large amount, the analytes may be adsorbed greatly resulting in an improvement in the detection sensitivity. In the conventional case, sufficient packing is difficult due to structural restrictions. Moreover, sufficient packing in the conventional case is difficult, because sufficient flow of an elution solvent is not possible, and the packing process itself is difficult. However, in exemplary embodiments of the present invention, the structure of the solid-phase preconcentration cartridge 10 is such that a loss of the length in the capillary 20 is not generated and a sufficient amount of the elution solvent may flow therethrough. Moreover, due to a tubing structure of the sleeve 30 which can be formed long enough, there is an advantage in that packing is performed very easily. In exemplary embodiments, it is noted that the elution solvent is injected at an outlet terminal 26 of the capillary 20 corresponding to the injection part 24. In conventional solid phase extraction, the elution solvent in injected in a direction where the sample flows through. However, in the case of injecting the elution solvent in a fashion as mentioned in exemplary embodiments, and to inject a sufficient amount of the elution solvent, the connection interface structure as mentioned above is very advantageous.

FIGS. 2a-2e are schematic diagrams illustrating principles of on-line automatic solid phase extraction coupled to nonaqueous capillary electrophoresis with applied field amplified sample stacking.

Figure 2A:
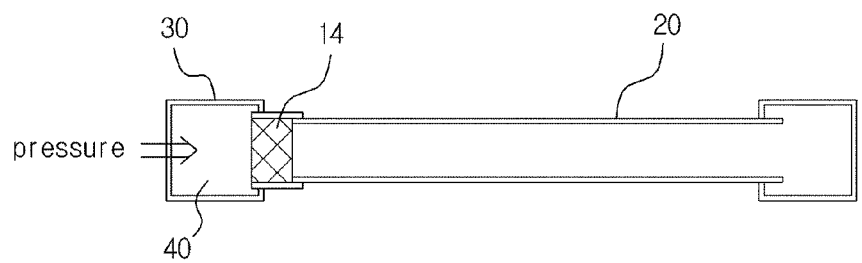
FIGS. 2a-2e are schematic diagrams illustrating principles of on-line automatic solid phase extraction coupled to non-aqueous capillary electrophoresis with applied field amplified sample stacking.

FIG. 2a shows a process of extracting a sample on a solid-phase preconcentration cartridge. The sample is continuously injected through a reservoir 30 connected at the injection part 24 of a capillary 20 to adsorb the sample 40 onto a solid-phase material 14. At this time, the unadsorbed substances are passed through, thereby allowing purification of the sample.

Figure 2B:
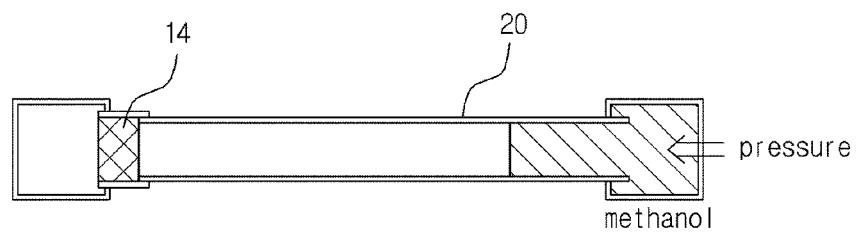

FIG. 2b shows a process of injecting an elution solvent (e.g., methanol), capable of eluting analytes adsorbed onto the solid-phase material 14, at the outlet terminal 26 of the capillary 20. In the typical solid phase extraction, the elution solvent is injected in a direction where the sample flows. However, in exemplary embodiments of the present invention, the elution solvent is injected at the outlet terminal 26 of the capillary 20. This allows automatic elution, and allows continuous stacking and analysis. Therefore, the extraction process becomes simplified, and rapid analysis becomes possible. In exemplary embodiments, a sufficient amount of the elution solvent may be used. By using the elution solvent in an amount to elute approximately all of the analytes adsorbed onto the solid-phase material, the problems generated from having the analytes remaining on the solid-phase material 14 is resolved. There may be a problem such that the electrophoretic ability is deteriorated due to decreased sample stacking efficiency. However, this problem can be resolved by the subsequent field amplified sample stacking.

Figure 2C:
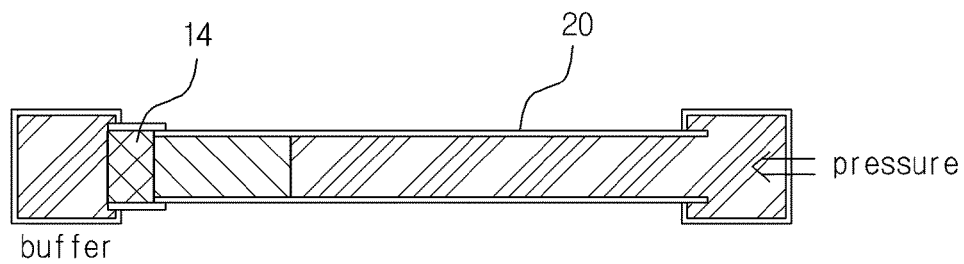

FIG. 2c shows a process of charging a nonaqueous buffer solution. The buffer solution made of methanol as a solvent is injected at the outlet terminal 26 of the capillary 20 to push the methanol to the solid-phase material 14.

Figure 2D:
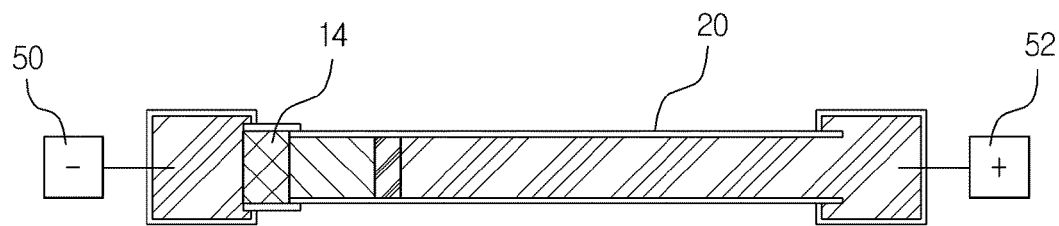

FIG. 2d shows a process of automatic elution and field amplified sample stacking. When an electric field is applied, the methanol solvent is passed through the solid-phase material 14 by electroosmosis and desorbs the adsorbed sample. The desorbed sample which has negative charge due to a cathode 50 is moved to the interface between methanol and the buffer solution at a anode 52. As the sample reaches the interface, the mobillity speed of the sample is decreased, and the sample is stacked at the interface.

Figure 2E:
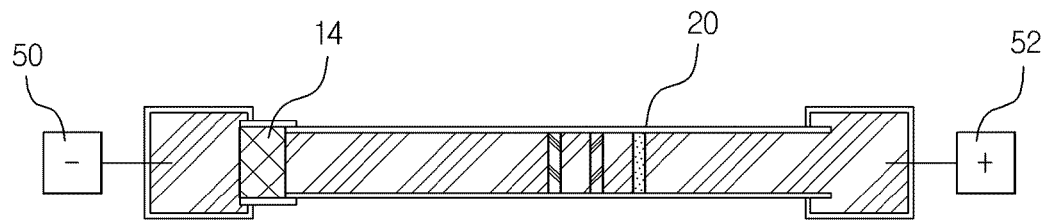

FIG. 2e shows a process of separating the sample in the nonaqueous buffer solution. After the entire organic elution solvent is passed through the capillary, the sufficiently stacked sample is separated for detection.

As shown in the above, example embodiments can perform elution, stacking and analysis automatically. Moreover, a joule heating problem is not generated due to a low conductivity of the nonaqueous buffer. Meanwhile, a large volume of the sample is used to extract a sufficient amount of the sample on the solid phase. Moreover, a large amount of the elution solvent is used to desorb the sample, and then the sample is stacked. Thus, the amount of desorbed sample is increased, thereby further improving the detection sensitivity. The exemplary embodiments of the above described methods can increase the sensitivity to several ten thousand-folds compared with a general aqueous capillary electrophoresis. Thus, the detection of the analytes is possible at a picomole level.

In addition, the constitution of the connection interface between the solid-phase preconcentration cartridge 10 and the capillary 20 provided in the exemplary embodiments is eligible to adopt the connection interface in the above-mentioned methods. The connection interface allows a use of the sample in a large volume such that a sample with low concentration can also be used. Moreover, since a large amount of the elution solvent can be used and a mobile time in the nonaqueous buffer can be sufficiently ensured, the electrophoretic ability can be improved.

A better understanding of exemplary embodiments will be described in more detail with reference to the following examples of applying the exemplary embodiments of the above-mentioned methods using a sample containing chlorophenol.

<Preparation of Solid-Phase Preconcentration Cartridge>

A sorbent and a frit are separated from SEP-PACK C18 cartridge (commercially available from Waters Corporation) and used. The frit is inserted into a 10 millimeters (mm) Teflon tubing having an internal diameter of 300 micrometers ($\mu$m) and an external diameter of 800 $\mu$m. Then, the sorbent is packed to have a thickness of 1 mm on the frit, and another frit is inserted to complete preparation of the solid-phase preconcentration cartridge. A capillary having an external diameter of 360 $\mu$m is inserted into the Teflon tubing to form a connection interface between the capillary and the solid-phase preconcentration cartridge.

<Improvement in Detection Sensitivity by Solid Phase Extraction and Field Amplified Sample Stacking>

To a 60 centimeter (cm) fused silica capillary having an internal diameter of 100 $\mu$m, a buffer solution at pH 8.0 made of methanol as a solvent and 25 mM Tris as an acetate was charged. A sample solution containing 50 nM of chlorophenol was injected at the injection part of the capillary to adsorb chlorophenol. Then, methanol was injected at 3 psi for 3 minutes at the outlet terminal of the capillary. Thereafter, the buffer solution was injected again at 3 psi for 48.5 seconds. The injection part and the outlet terminal of the capillary was immersed in the buffer solution, and an electric field of 30 kV was applied to desorb and stack the sample.

COMPARATIVE EXAMPLE

100 $\mu$M of chlorophenol was analyzed by conventional capillary electrophoresis. A buffer solution made of water as a solvent and 25 mM borate was used. The sample was injected at 0.2 psi for 3 seconds.

Figure 3A:
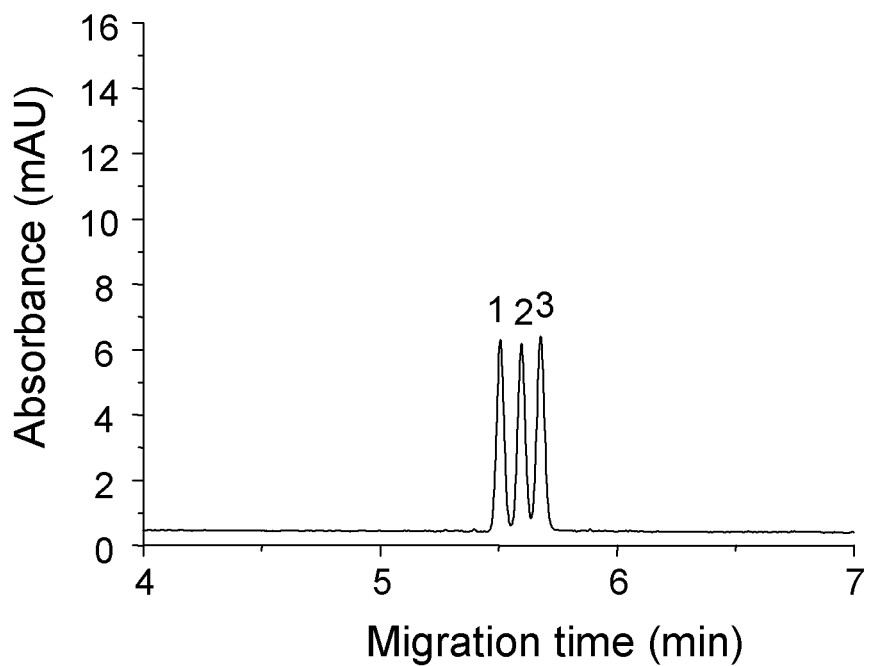
FIG. 3a is a graph illustrating the analytic results of 100 μM sample subjected to general capillary electrophoresis and FIG. 3b is a graph illustrating the analytic results of 50 nM of chlorophenol according to an exemplary embodiment of the present invention.
Figure 3B:
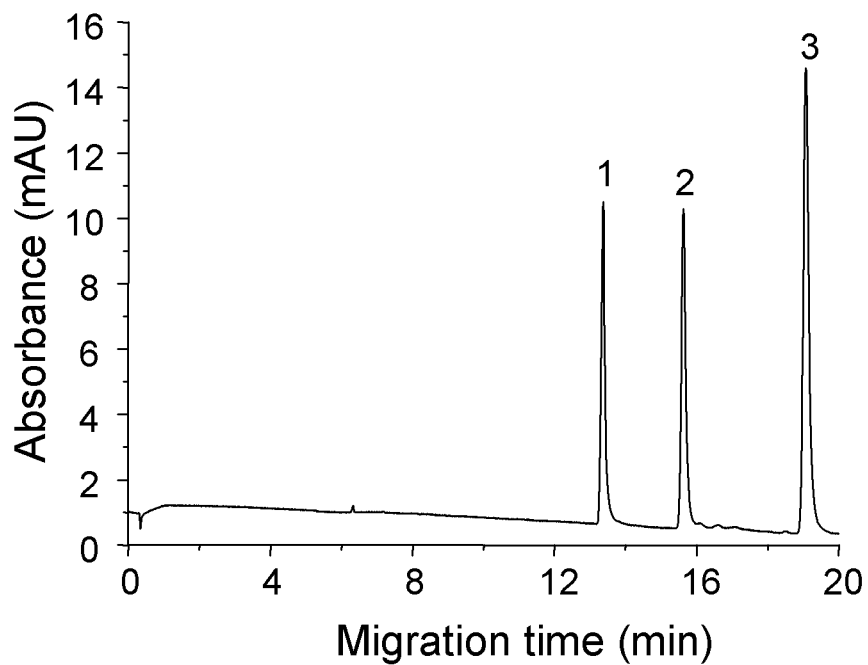

FIG. 3a shows the analytic results of 100 $\mu$M sample subjected to general capillary electrophoresis. FIG. 3b is a graph illustrating the analytic results of 50 nM of chlorophenol according to exemplary embodiments of the present invention. 1 is pentachlorophenol, 2 is 2,3,5,6-chlorophenol, and 3 is 2,3,4,6-chlorophenol. As shown in FIG. 3b, 16,000 to 20,000-folds stacked result can be obtained.

While the present invention has been shown and described with reference to some exemplary embodiments thereof, it should be understood by those of ordinary skill in the art that various changes in form and detail may be made therein without departing from the spirit and scope of the present invention as defined by the appending claims.

What is claimed is:

1. An interface structure between a solid-phase preconcentration cartridge and a capillary for analyzing a sample by coupling solid phase extraction to capillary electrophoresis, wherein the solid-phase preconcentration cartridge comprises:
   a polytetrafluoroethylene tubing sleeve, the sleeve being packed with a solid-phase material at one end;
   an injection part of the capillary inserted into the other end of the tubing sleeve where the sample is injected into the tubing sleeve; and
   wherein the capillary is the only capillary inserted into the tubing sleeve and further wherein the interface structure is positioned such that the full length of the capillary, other than the injection part of the capillary inserted into the tubing sleeve, protrudes from the tubing sleeve.

2. The structure of claim 1, wherein the capillary inserted into the tubing sleeve has a length at least 3 times an outer diameter of the capillary.

3. The structure of claim 1, wherein an inner diameter of the tubing is smaller than an outer diameter of the capillary to be inserted.

* * * * *